United States Patent
Edwards et al.

(10) Patent No.: US 9,849,233 B1
(45) Date of Patent: Dec. 26, 2017

(54) DISPOSABLE INFUSION PUMP SYSTEM FOR AMBULATORY PATIENTS

(71) Applicants: Oliver J. Edwards, Ocoee, FL (US); Justin J. Zdeb, Apopka, FL (US)

(72) Inventors: Oliver J. Edwards, Ocoee, FL (US); Justin J. Zdeb, Apopka, FL (US)

(73) Assignee: NOVUS MEDICAL PRODUCTS, INC., Apopka, FL (US)

( * ) Notice: Subject to any disclaimer, the term of this patent is extended or adjusted under 35 U.S.C. 154(b) by 0 days.

(21) Appl. No.: 15/591,222

(22) Filed: May 10, 2017

(51) Int. Cl.
| *A61M 5/145* | (2006.01) |
| *A61M 5/142* | (2006.01) |
| *F04B 43/02* | (2006.01) |
| *F04B 53/16* | (2006.01) |

(52) U.S. Cl.
CPC .... *A61M 5/14224* (2013.01); *A61M 5/14244* (2013.01); *F04B 43/02* (2013.01); *F04B 53/16* (2013.01); *A61M 2205/583* (2013.01); *A61M 2209/088* (2013.01)

(58) Field of Classification Search
CPC ..... F04B 43/02; F04B 45/04; A61M 5/14224; A61M 5/14586; A61M 5/1493; A61M 1/1037; A61M 1/306; B65D 83/0061
See application file for complete search history.

(56) References Cited

U.S. PATENT DOCUMENTS

| | | | | | |
|---|---|---|---|---|---|
| 3,468,308 | A | * | 9/1969 | Bierman | A61M 5/152 |
| | | | | | 128/DIG. 12 |
| 3,894,538 | A | * | 7/1975 | Richter | A61M 5/14276 |
| | | | | | 204/627 |
| 3,991,763 | A | * | 11/1976 | Genese | A61M 1/0011 |
| | | | | | 604/133 |
| 4,318,400 | A | * | 3/1982 | Peery | A61M 5/141 |
| | | | | | 128/DIG. 12 |
| 4,437,590 | A | * | 3/1984 | LaBruna | F02K 9/605 |
| | | | | | 222/386.5 |
| 5,045,064 | A | * | 9/1991 | Idriss | A61M 5/14276 |
| | | | | | 128/DIG. 12 |
| 5,090,963 | A | * | 2/1992 | Gross | A61M 5/155 |
| | | | | | 128/DIG. 12 |
| 5,167,631 | A | * | 12/1992 | Thompson | A61M 5/152 |
| | | | | | 222/386.5 |
| 5,171,301 | A | * | 12/1992 | Vanderveen | A61M 5/168 |
| | | | | | 604/141 |
| 5,242,406 | A | * | 9/1993 | Gross | A61M 5/155 |
| | | | | | 128/DIG. 12 |

(Continued)

*Primary Examiner* — Matthew F Desanto

(57) ABSTRACT

An infusion pump comprises an elastomeric hemispheric deformable rolling diaphragm, an external rigid housing with internal area no greater than that of the rolling diaphragm exterior, and a rigid cap structure which sealingly fastens the rim of the rolling diaphragm to the rim of the external housing. Thickness of the flexing wall of the diaphragm is tapered from rim to a region on the central axis to provide approximately constant pressure as the pump empties its contents. The rigid housing has an port in its center opposite its rim to allow insertion of fluid to roll the diaphragm inward, and to allow outflow of the stored pressurized fluid as desired. The housing and/or cap structure may have an external belt mounting fixture to facilitate donning the infusion pump for ambulatory users. The simplified design enables low manufacturing cost and hence single-use disposability.

13 Claims, 6 Drawing Sheets

(56) References Cited

U.S. PATENT DOCUMENTS

| | | | | |
|---|---|---|---|---|
| 5,306,257 A | * | 4/1994 | Zdeb | A61M 5/14586 604/131 |
| 5,368,570 A | * | 11/1994 | Thompson | A61M 5/1408 604/131 |
| 5,431,634 A | * | 7/1995 | Brown | A61M 5/14224 417/413.1 |
| 6,200,293 B1 | * | 3/2001 | Kriesel | A61M 5/14248 128/DIG. 12 |
| 6,245,042 B1 | * | 6/2001 | Kriesel | A61K 9/0004 604/132 |
| 6,258,063 B1 | * | 7/2001 | Haar | A61M 5/2425 222/633 |
| 2011/0172638 A1 | * | 7/2011 | Moga | A61M 5/14224 604/506 |
| 2014/0350510 A1 | * | 11/2014 | Carlisle | A61M 5/155 604/500 |

* cited by examiner

US 9,849,233 B1

DISPOSABLE INFUSION PUMP SYSTEM FOR AMBULATORY PATIENTS

FIELD OF THE INVENTION

This invention relates to liquid dispensing apparatus and pertains particularly to an improved infusion apparatus or assembly for dispensing liquid medication to a patient at a controlled constant delivery rate: small enough to enable patient ambulation, and simplified in design to be affordably single-use and disposable.

BACKGROUND: DESCRIPTION OF RELATED ART

It is often necessary to intravenously supply patients with pharmaceutically active liquids at a controlled rate over a long period of time. There are many applications in academic, industrial and medical fields as well as others, that benefit from devices and methods that are capable of accurately and controllably delivering fluids, including liquids that have a beneficial effect when administered in known quantities at controlled rates. This is particularly true in the medical field where treatments for many patients include the administration of a known amount of a substance at predetermined intervals. It is often desirable that this be accomplished while the patient is in an ambulatory state. A few devices have been developed in the past for accomplishing this purpose.

Prior art disposable devices typically incorporate an inflatable elastomeric balloon-like bladder forming a liquid container, with an exit flow restriction device and tubing (intravenous, or IV) for transfer of the liquid to the patient. The walls of the bladder stretch and expand when filled with the liquid, and in tension provide pressure for expelling the liquid. These prior art devices are typically filled by hand syringe and generally require excessive force to initiate the filling: it is difficult to insert an initial volume in conventional inflatable elastomeric bladders. From such balloon-bladders the pressure and flow rates typically varies widely through the course of expelling the fluid and infusing the patient, and they characteristically exhibit a rapid rise in flow rate as the balloon-device nears completion of delivery. Further, such conventional bladders have a history of many reported occasions of inflated-bladder rupture. In addition, they typically leave a significant undispensed residual volume: wasting costly pharmaceuticals.

Various materials are used for constructing conventional inflatable elastomeric bladders, including natural rubber. Construction typically requires several layers of material. The use of silicone in tubular form to function as an elastic pressurized liquid reservoir for infusion purposes is described in U.S. Pat. No. 4,909,790; this discloses an infusion device using tubular bladders mounted on mandrel supports with downstream restrictors to deliver uniform flow rates. Another example may be found in U.S. Pat. No. 7,704,230 which describes a similar pressurized fluid reservoir made from a silicone tube for an infusion system. Prior art references point to numerous possible combinations of silicones, structural dimensions, filling pressures, operating pressures, and fill volumes. However, limitations of this expandable-bladder prior art are exemplified by the performance of the silicone tube as disclosed in U.S. Pat. No. 7,704,230. The described performance is inferior because of the variability in flow rate and pressure during the infusion period, and the difficulty in dispensing substantially all of the liquid by the end of the infusion period.

Another approach to controlled infusion has been mechanical infusion pumps. In prior art, vacuum-driven or spring-driven syringe devices have been employed to create the desired fluid pressure. A typical disposable spring infuser compresses a contained bag to expel the medication. The compressed-spring mechanism squeezes the medication out of the container and through the flow-restriction device and the IV line to the patient. Since the spring pressure will decrease as the spring extends, the infusion rate will perforce decrease as the infusion proceeds.

Other prior art in infusion pumps includes electronic pumps: typically costly, non-disposable, and requiring meticulous cleaning between cycles. These are in general unsuitable for ambulatory patients.

Therefore, there is a need for a simple fluid infusion pump that is small enough to be worn by ambulatory patients, that delivers the fluid at a constant flow rate, that exhibits no burst of flow near the end of delivery, that expels essentially all of the costly fluid, and that is low enough in manufacturing cost to enable it to be single use: optionally pre-filled and disposable when the delivery is complete.

SUMMARY OF THE INVENTION

Systems and methods for dispensing and infusing fluids at a controlled and constant rate are disclosed. The problems described above are addressed by the present invention of an improved elastomeric pump for an infusion assembly.

The pump comprises three basic elements:

(a) an elastomeric, approximately hemispherical, hollow rolling diaphragm body, convex toward the liquid to be expressed, having a circular peripheral rim diameter and an opposed end, said body having uniform wall thickness in a circumference parallel to the periphery, and decreasing in wall thickness along the orthogonal direction to its opposed end. As fluid pressure is imposed on its outer surface, the hemispheric diaphragm is forced to roll inward, and inverts increasingly as additional fluid is impressed.

The elastomeric material is desirably a synthetic rubber, with a Shore hardness (durometer) of approximately 65 A to 78 A: near that of natural rubber.

According to the present invention, the introduction of a volume of liquid between a contiguous outer housing and the diaphragm body pressurizes and expands the space between them as the elastomeric body compresses and curls inward, inverting toward its rim. The pump subsequently dispenses substantially all the volume of liquid through the liquid inlet/egress port upon rolling restoration of the diaphragm to its preloaded (relaxed) geometry; the relaxed diaphragm fills the volume of the outer housing. The volume of liquid that can be pumped is approximately equal to the volume of the "bowl" cavity of the outer housing.

According to an aspect of the invention, the thickness of the wall of the elastomeric diaphragm body, and hence its flexural strength, varies from the rim to the opposed end, with said variation at a particular circular sector of the body having an effect of modifying the fluid pressure as that sector is un-flexed to return to its relaxed shape. The local thickness of the elastomeric flexure walls varies from a maximum at the rim to a minimum at the opposed end. After extensive experimentation, the optimum taper geometry has been found to be as follows: In order to maintain a near-constant pressure on the remaining fluid as the diaphragm unrolls, the wall thickness profile is defined by translating the profile of the exterior toward the central axis by a distance equal to the rim thickness of the diaphragm. In graphic cross-section design, the geometry of the curved external wall of the hemispheric diaphragm is translated toward the central axis by a distance equal to the peripheral thickness of the diaphragm, to generate the tapered profile of the diaphragm wall. A small circular sector in the end opposite the rim is made uniform in thickness, for diaphragm integrity.

(b) The rolling diaphragm is contained in a rigid containment vessel: an outer housing whose interior geometry matches (is contiguous to) that of the outer geometry of the diaphragm body when it is relaxed, i.e., completely unrolled. As fluid is introduced through an inlet port at the opposed end of the outer housing, the diaphragm flexes and rolls inward, and inverts increasingly as the fluid fills the pump containment. The peripheral rim diameter of the elastomeric diaphragm body is sealingly secured to the rim diameter of the outer housing. The inlet port is centrally located in the opposed end of the housing, into which fluid is passed to deform the flexure diaphragm into an inverted concavity, and out of which the pressurized fluid is passed as the rolling diaphragm returns to its preloaded, relaxed shape, contiguous with the outer housing wall.

The outer housings are constructed with a medical grade polymer that is UV and sterilization resistant, which after sterilization will maintain its material strength, and color or clarity.

The inner surface of the outer housing is flattened in a central circular area at its opposed end. This serves to prevent the diaphragm from fully relaxing and thus prevents any terminal pulse in pressure, and correspondingly serves to lower the initial pressure required in filling the pump. This "stop" preventing the final pressure/flow pulse from the diaphragm roll-out may alternately be replaced or augmented by one or more short pins or surface bumps in the housing, adjacent the outlet port, to prevent the complete relaxation of the diaphragm opposed end and thus prevent a terminal pulse in pressure and flow, and also to present an expanded exposed surface about the port for lower initial pressure on filling the pump. Thus, to initiate the bellows roll, radial grooves or surface bumps are used to allow the immediate spread of the initiating pressure over the flattened area.

(c) A rigid outer housing cap having a U-shaped cross section in its upper rim is used to assemble the outer housing to the inner elastomeric rolling diaphragm. After the diaphragm bowl is inserted into the mating geometry of the outer housing, the outer housing cap is attached, with the inner lip of its U-shape pressing radially outward to compress the rim of the elastomer bowl. Thus the outer housing cap compressively seals the rim of the inner diaphragm body to the rim of the outer housing. The outer housing cap may be secured to the outer housing by means of mating threads, or bayonet mount, or preferably: by snap-fit joint attachment to enable rapid manufacturing assembly.

Generally speaking, the present invention relates to the discovery of certain relative ratios of diaphragm wall thickness and liquid fill volumes that result in specific pressure ranges for the purpose of infusing liquid at uniform flow rates until substantially all the liquid is expelled. According to an aspect of the invention, the expansion of the diaphragm to contain a given fill volume (e.g., 50-600 milliliters) may be readily accomplished by manual injection from a syringe device (filling pressure typically less than 20 psig). In another aspect of the invention, there is minimal residual volume of liquid in the pump after completion of the infusion. In another aspect of the invention, the fill volume of liquid is delivered at a substantially uniform flow rate at designed-in pressures of typically 5 to 8 psig (as measured at the input/output port). In another aspect of the invention, the wall the rolling-bellows pump—operating in compressive flexure rather than tensile stress—will not exhibit rupture on filling, as so often happens with the use of stretching balloon infusion pumps.

Other objects, advantages and applications of the present disclosure will be made clear by the following detailed description of a preferred embodiment of the disclosure and the accompanying drawings wherein reference numerals refer to like or equivalent structures.

DETAILED DESCRIPTION OF THE INVENTION

Figure 1A:
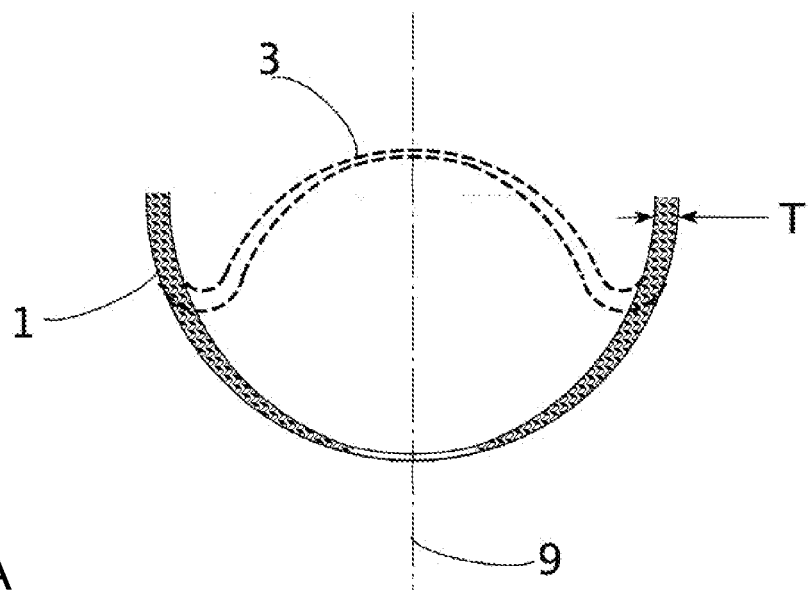
FIG. 1A is a section view of an embodiment of the rolling diaphragm in its released state and also (in dotted lines) in its rolled or compressed state.

Provided herein are systems, devices and methods for dispensing fluids at a preset constant pressure and/or flow rate through a flow restrictor. The advances may allow for a safer and more accurate delivery of medicament to a patient than is currently attainable today from other devices, systems, and methods. The advances may allow for a lower manufacturing cost, and thus for an expendable or single-use device. Device and method embodiments discussed herein may be used for insulin, pain medication, chemotherapy, iron chelation, immunoglobulin treatment, dextrose or saline IV delivery, or any other suitable indication or application. Non-medical applications are also contemplated.

Reference will now be made in detail to one or more embodiments, examples of which are illustrated in the drawings. It should be understood that features may be used or combined in many other configurations to yield a still further new embodiment.

Figure 1B:
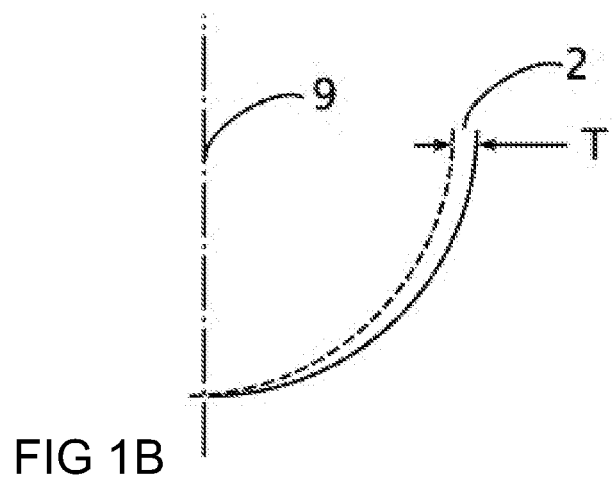
FIG. 1B is a schematic section view of one half of the elastomeric rolling diaphragm

FIGS. 1A and 1B show a cross section of an approximately hemispherical elastomeric rolling diaphragm. FIG. 1A shows the cross section of the diaphragm 1, as molded. The thickness T of the diaphragm wall is locally determined by the desired pressure of the pump when the pump is filled and the diaphragm deformed and rolled into its inverted position 3. In this pump, the desired pressure is exerted by the flexural resistance of the elastomeric walls, rather than by tensile stress of prior art infusion pumps.

Referring to FIG. 1B, the geometry of the diaphragm wall thickness is determined by translating the geometry of the rounded external wall inward toward the central axis of the diaphragm by a distance equal to the thickness T of the peripheral rim 2. This thins the walls as appropriate to render the pressure near-constant as the diaphragm unrolls and expels the fluid.

Figure 1C:
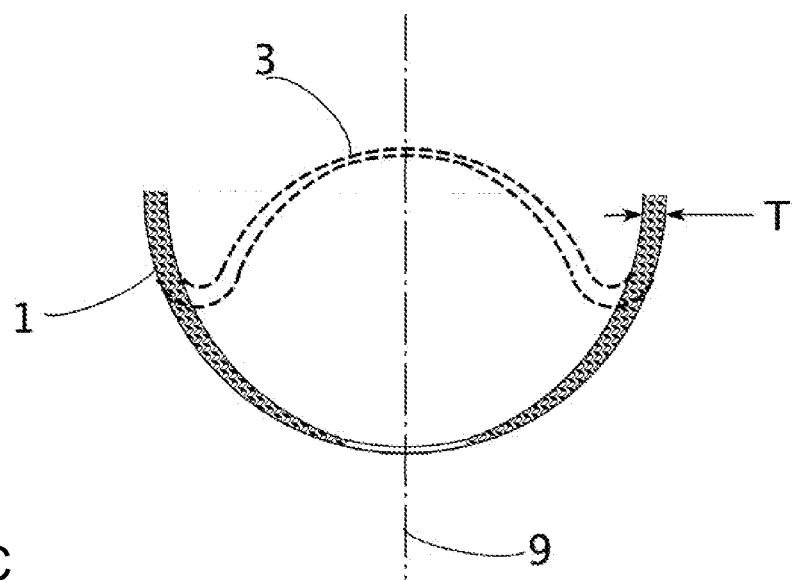
FIG. 1C is a section view of the completed elastomeric diaphragm member, ready for installation.

FIG. 1C shows a completed elastomeric diaphragm 1 as molded, with an extended constant-thickness rim extension 5 terminated by an attachment lip 6. Optionally, one or more circumferential raised ribs 8 may be added to enhance the sealing of the diaphragm against the inner wall of the outer housing.

The rim of the outer housing may be extended at constant diameter 9 to provide an external surface for threads 10 for mounting an assembly cap, or alternately for teeth 11 to enable snap-on or bayonet mounting of said cap.

Figure 2A:
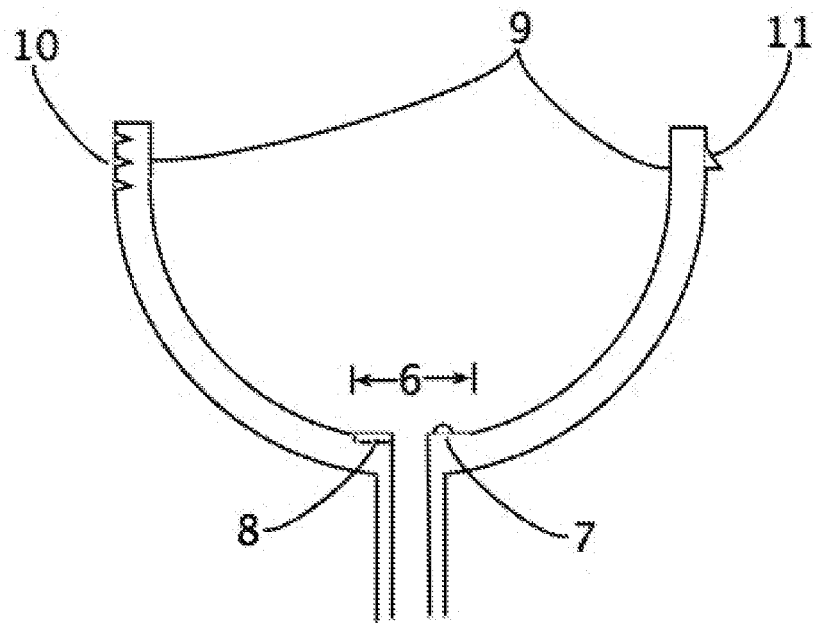
FIG. 2A is a section view of a rigid outer housing of substantially hemispheric internal geometry.
Figure 2B:
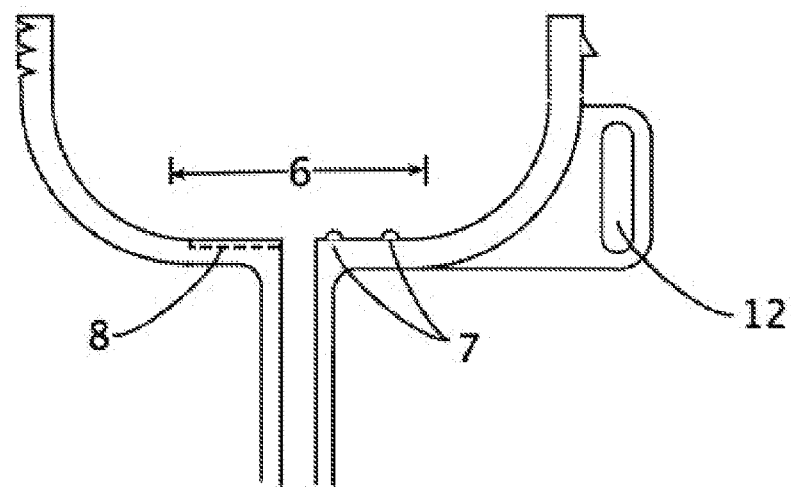
FIG. 2B is a section view of a rigid outer housing of arbitrary internal geometry.

For some embodiments it may be desirable to have the inner surface of the outer housing depart considerably from a hemisphere, as illustrated in FIG. 2B. Here the flattened central area 6 is enlarged. The inner contour of the outer housing may be modified as desired, as long as the area of the inner surface of the outer housing does not exceed the corresponding area of the diaphragm. Thus, the relaxed diaphragm will remain contiguous with the non-hemispheric outer housing; there will be no residual space between the elastomeric and the rigid outer wall.

For some embodiments it may be desirable to include a belt or sash mounting fixture 12 on the outer housing, to facilitate donning the infusion pump for ambulatory users.

For some embodiments it may be desirable to make the external housing of a transparent material, with the inner elastomeric diaphragm marked by printed or molded symbols to meter or visually indicate the amount of fluid left in the pump assembly during infusion.

Figure 2C:
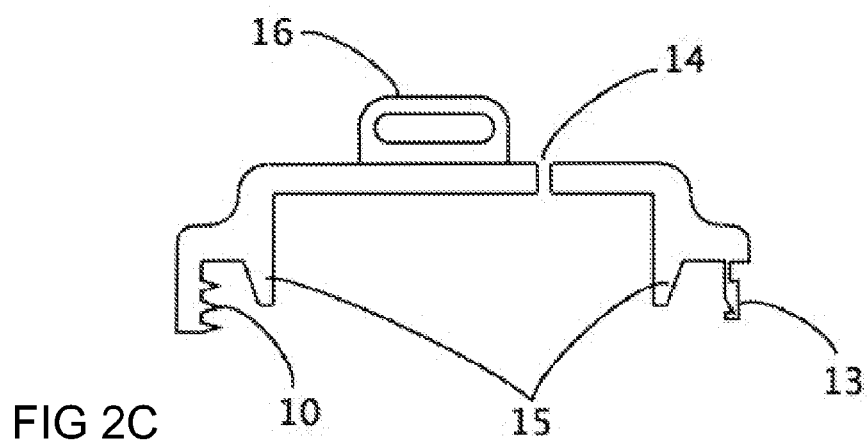
FIG. 2C is a section view of a cap structure

FIG. 2C shows a cap structure for assembling and sealing the diaphragm component to the outer housing. It may attach to the outer housing by threaded interface 10. Alternately it may use a bayonet mount structure. Preferably the attachment interface may be implemented by use of a tooth structure 13 for annular or incremental snap-on fit, to obtain most rapid assembly.

The cap structure may be open in the form of a ring, or it may be solid. In the case of a solid cap, an aperture 14 must be added, to allow air passage on pump fill and emptying. An annular wedge element 15 is added to the underside of the cap, forming a U-shape with the tooth structure 13. This element 15 serves at assembly to radially compress the circumferential rim of the elastomeric diaphragm, sealingly attaching the diaphragm to the interior rim of the outer housing.

For some embodiments it may be desirable to include a belt or sash mounting fixture 16 on the cap structure, to facilitate donning the infusion pump for ambulatory users.

Figure 3:
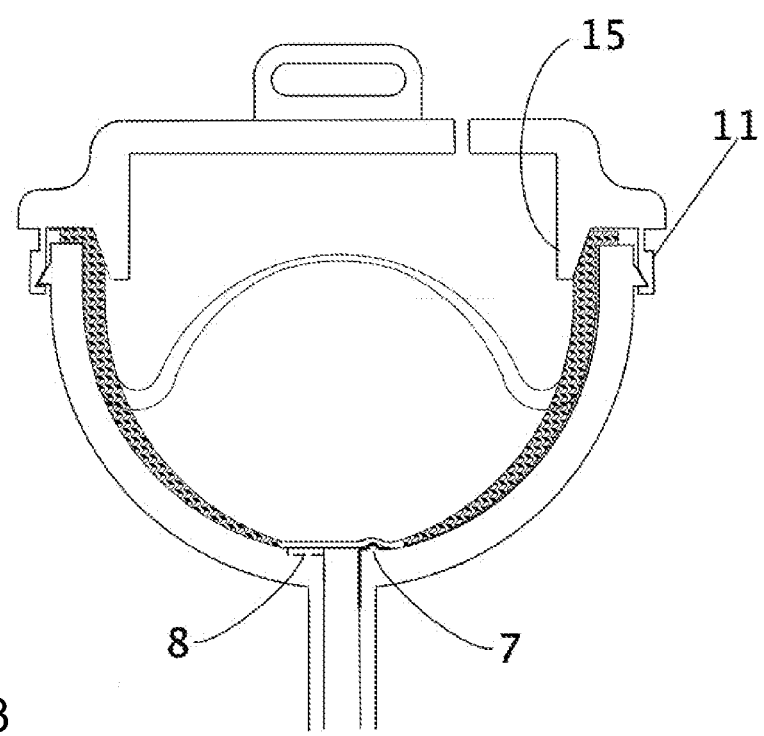
FIG. 3 is a section view of an assembled infusion pump

In final assembly, the elastomeric diaphragm is seated in the outer housing to be contiguous with its inner surface, and the cap is snapped or screwed onto the outer housing. The assembled pump is show in cross section in FIG. 3, illustrated here with snap fittings.

The rim of the elastomeric diaphragm is compressed radially outward by the inserted taper of the annular wedge element 15 to form an attachment point and a strong seal between the outer surface of the diaphragm and the inner surface of the outer housing.

A flattened sector in the center of the opposed end of the housing structure flattens the central portion of the diaphragm, and small bumps or posts 7 (illustrated on the right) or alternate small radial grooves 8 in the flat portion (illustrated on the left) expose that flat disc of the elastomeric diaphragm to allow filling without an initial pulse of backpressure or a terminal pressure pulse on emptying.

Figure 4:
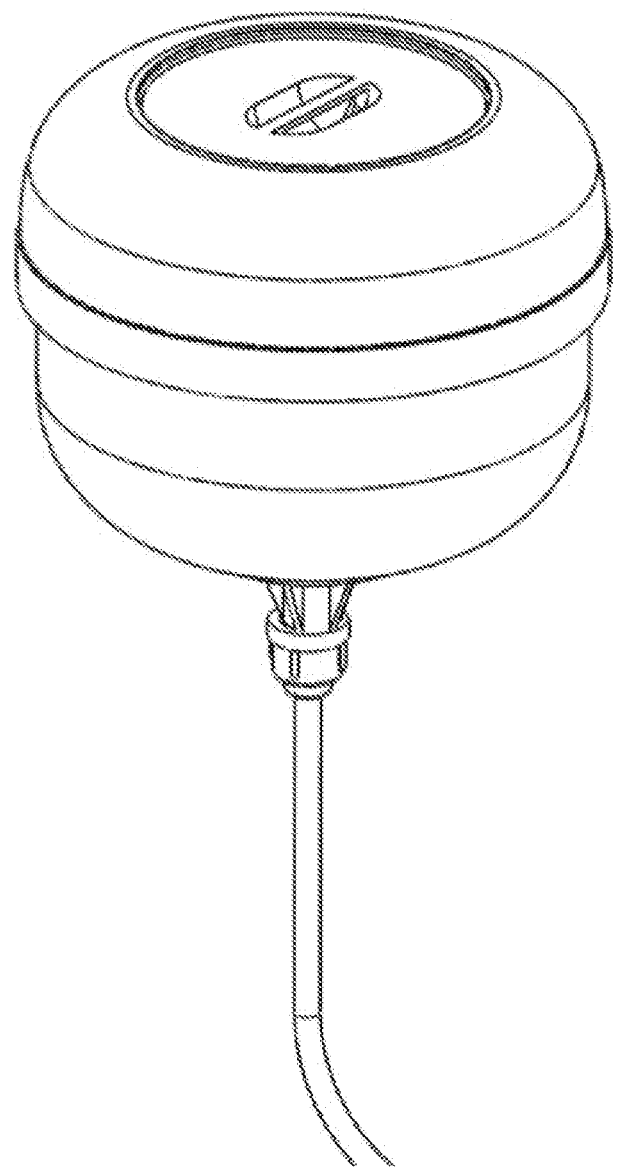
FIG. 4 is an external view of the assembled pump, with flow controller and tubing attached, and with support strap through the top or side.

FIG. 4 is an external view of the assembled pump with IV tubing attached, and with sash mounting fixture here shown integrated in the top of the pump.

Figure 5:
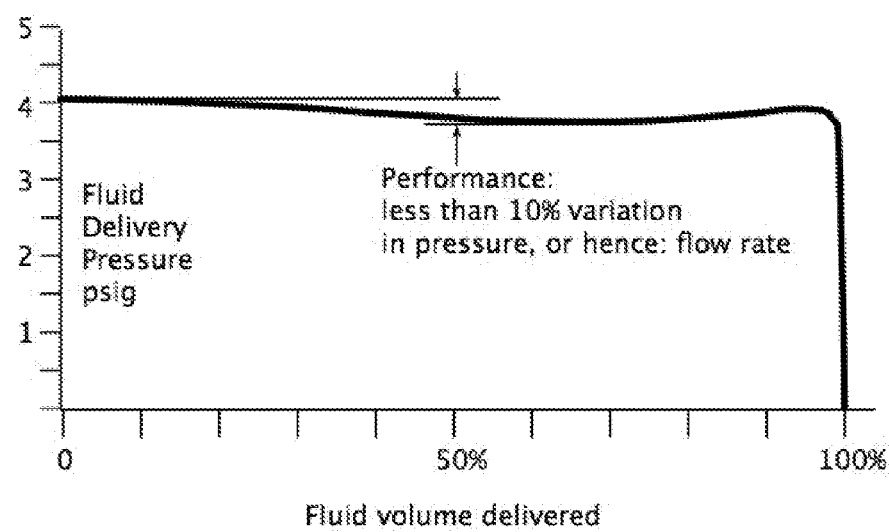
FIG. 5 is a graph of the performance of a typical pump according to this teaching.

FIG. 5 shows a graph of the performance of a typical infusion pump made according to this teaching. The pressure is measured as a function of the fraction of total fluid delivered in a single pump cycle. Notable is the constancy of pressure and resultant flow rate, and the absence of any significant pressure spike at the end of infusion. Correspondingly no abnormal force needed to initiate filling the pump.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion system, comprising:
    an elastomeric hollow flexural diaphragm body of approximately hemispheric shape, wherein the elastomeric diaphragm body has a rim, an opposed end and a wall thickness that decreases from the rim to the opposed end, said wall thickness geometry being defined by translation of an outer contour toward a central axis by a distance equal to a thickness of the rim, said wall thickness further being made constant over a central area opposed to the rim;
    a rigid outer housing with interior of approximately hemispheric shape, said interior of the outer housing has an area not exceeding an area of an outer surface of the elastomeric diaphragm body, and said outer housing has an input/output port;

wherein the input/output port is surrounded by a multiplicity of small bumps or posts having a height between 0.010 to 0.060 inches on an inner surface of the outer housing and said small bumps or posts are configured to separate the outer surface of the elastomeric diaphragm body from the inner surface of the outer housing;

and a cap structure that sealingly attaches the rim of the elastomeric diaphragm body to the interior of the outer housing.

2. The ambulatory infusion system of claim 1, wherein the rim of the flexural diaphragm body is extended at uniform thickness to provide an attachment section.

3. The ambulatory infusion system of claim 2, wherein the rim of the flexural diaphragm body is terminated by an integral larger diameter ring providing a location and sealing surface.

4. The ambulatory infusion system of claim 2, wherein one or more circumferential raised ribs are added to an exterior of the rim of the flexural diaphragm body to provide enhanced sealing.

5. The ambulatory infusion system of claim 1, wherein the contour of the interior of the outer housing is made substantially flat over a circular area that is concentric with the axis of symmetry.

6. The ambulatory infusion system of claim 1, wherein the cap structure attaches to the outer housing by thread means, bayonet mounting means, or snap-fit means.

7. The ambulatory infusion system of claim 1, wherein the cap structure includes a conically tapered interior structure that, when the cap is pressed onto the outer structure, will radially compress the elastomeric rim outward to seal and attach said rim to the interior of the outer housing.

8. The ambulatory infusion system of claim 1, wherein the outer housing is made from a transparent material and the inner elastomeric diaphragm is marked by printed or molded symbols to visually indicate the amount of fluid remaining in the pump assembly during infusion.

9. The ambulatory infusion system of claim 1, wherein the outer housing includes an external belt or sash mounting fixture, to facilitate donning the infusion pump for ambulatory users.

10. The ambulatory infusion system of claim 1, wherein the cap structure includes an external belt or sash mounting fixture, to facilitate donning the infusion pump for ambulatory users.

11. The ambulatory infusion system of claim 1, wherein the flexural diaphragm is comprised of one or more of polyisoprene, polychloroprene, silicone rubber, and natural rubber.

12. The ambulatory infusion system of claim 1, wherein the outer housing is comprised of one or more of polypropylene, polyetheretherketone, polycarbonate, polysulfone, polyvinylchloride or polystyrene.

13. An ambulatory infusion system comprising:

an elastomeric hollow flexural diaphragm body of approximately hemispheric shape, wherein the elastomeric diaphragm body has a rim, an opposed end and a wall thickness that decreases from the rim to the opposed end, said wall thickness geometry being defined by translation of an outer contour toward a central axis by a distance equal to a thickness of the rim, said wall thickness further being made constant over a central area opposed to the rim;

a rigid outer housing with interior of approximately hemispheric shape, said interior of the outer housing has an area not exceeding an area of an outer surface of the elastomeric diaphragm body, and said outer housing has an input/output port;

wherein the input/output port is surrounded by a multiplicity of radial grooves on an inner surface of the outer housing having a depth between 0.010 to 0.080 inches and said radial grooves are configured to separate the outer surface of the elastomeric diaphragm body from the inner surface of the outer housing;

and a cap structure that sealingly attaches the rim of the elastomeric diaphragm body to the interior of the outer housing.

* * * * *